United States Patent [19]
Schwartz

[11] Patent Number: 5,626,149
[45] Date of Patent: May 6, 1997

[54] MEDICATION DISPENSING FACILITATION SHEATHS AND METHODS OF USE THEREOF

[76] Inventor: Alan N. Schwartz, 19211 - 93rd Pl. West, Edmonds, Wash. 98020

[21] Appl. No.: 619,372

[22] Filed: Mar. 21, 1996

Related U.S. Application Data

[63] Continuation-in-part of Ser. No. 912,683, Jul. 13, 1992, Pat. No. 5,513,652.

[51] Int. Cl.⁶ .................................................... A61F 6/02
[52] U.S. Cl. ........................................ 128/842; 600/38
[58] Field of Search ................................. 128/842, 844, 128/918; 604/347–353; 600/38–40

[56] References Cited

U.S. PATENT DOCUMENTS

| | | | |
|---|---|---|---|
| 2,410,460 | 11/1946 | Robinson | 128/844 |
| 2,577,345 | 12/1951 | McEwen. | |
| 2,586,674 | 2/1952 | Lonne. | |
| 3,136,417 | 6/1964 | Clinch. | |
| 4,415,548 | 11/1983 | Reddy. | |
| 4,432,357 | 2/1984 | Pomeranz. | |
| 4,446,860 | 5/1984 | Gutnick | 128/844 |
| 4,498,466 | 2/1985 | Pomeranz. | |
| 4,564,006 | 1/1986 | Pomeranz. | |
| 4,798,600 | 1/1989 | Meadows. | |
| 4,829,991 | 5/1989 | Boeck | 128/844 |
| 4,840,188 | 6/1989 | Heidenfelder. | |
| 4,919,149 | 4/1990 | Stang | 128/844 |
| 5,046,489 | 9/1991 | Gibson | 128/844 |
| 5,137,032 | 8/1992 | Harmon. | |
| 5,333,621 | 8/1994 | Denzer. | |

*Primary Examiner*—Michael A. Brown
*Attorney, Agent, or Firm*—Graybeal Jackson Haley LLP

[57] ABSTRACT

Erectile function facilitators and methods of use thereof wherein an open-ended elastic sheath has at least one fluid retaining chamber incorporated therein and has means for initially partitioning and for subsequently providing communication between said at least one fluid retaining chamber and the interior of said elastic sheath such that fluid in said fluid remaining chamber can be dispensed into the interior of said sheath by the application by the wearer of external pressure to at least one fluid retaining chamber. The wearer has complete control as to the time and extent of medication being dispensed. Partitioning and subsequent communication between the fluid retaining chamber and the sheath interior can be by means of valves or stretchable membrane, or by fold or twist or clamping, as desired.

9 Claims, 2 Drawing Sheets

MEDICATION DISPENSING FACILITATION SHEATHS AND METHODS OF USE THEREOF

CROSS REFERENCE TO RELATED APPLICATIONS

This application is a continuation-in-part of my application my Ser. No. 07/912,683 entitled Male Erection Facilitation Sheaths and Methods of Using Same, filed Jul. 13, 1992, and which issued as U.S. Pat. No. 5,513,652 on May 7, 1996.

FIELD OF INVENTION

The invention pertains to devices and methods for assisting erectile function. More, specifically to devices which are sheaths designed for dispensing medication in connection with erection facilitation, and to methods of use thereof.

BACKGROUND OF INVENTION

Normal male erectile function requires numerous physiologic events to occur in concert. First, adequate neuropsychogenic, chemical or electrical stimulus must be present. Second, there must be adequate arterial blood inflow into the penis. Third the corporal, smooth muscles must relax and the corporal epithelial tissue must respond to the erectile stimulus, thus allowing the corporal sinusoids to expand and fill with blood. Finally, the venous closure mechanism must be initiated to prevent outflow of blood, thus resulting in storage of blood within the penis.

Failure of any one of these mechanisms results in erectile dysfunction. A number of vasoactive pharmaceutical agents, one of them papaverine, for example, can be used to stimulate and maintain erections by compensating for the defective mechanism.

Application of vasodilators is now accepted as a method for clinically producing erections. Effective vasodilators such as papaverine hydrochloride can be directly injected by needle into the corpus of the penis. A system for dispensing vasodilator medications such as nitroglycerine exists which utilize transdermal creams and patches. There is a need for a device and a method which can deliver transdermal medication safely and effectively for individuals requiring multiple doses and requiring doses of different strength. There is a need for dispensing medication at different time intervals during intercourse in order to maintain and sustain adequate erections.

PRIOR ART

U.S. Pat. No. 3,136,417 of Clinch discloses a method for treating the surface of a condom with a lubricant. U.S. Pat. No. 4,415,548 of Reddy discloses a condom saturated with spermicidal solution. U.S. Pat. No. 5,137,032 of Harmon discloses a condom in which a lubricant may be introduced into the sealed condom when it is packaged. U.S. Pat. No. 4,829,991 of Boeck discloses an elastic sleeve-like member that is coated by a transdermal vasodilator applied sporadically or uniformly. U.S. Pat. No. 5,333,621 of Denner discloses a vasodilator delivery system using transdermal patches. U.S. Pat. No. 4,840,188 discloses a condom with a desensitizing coating at the closed end of the condom. U.S. Pat. Nos. 3,136,417, 4,415,548, 5,137,032, 4,829,991, 5,333,621, and 4,840,188 disclose condoms that are coated with or lined by medication, with no means for storing or delivering a varied amount of medication. There is no method disclosed in these patents of a fluid retaining chamber for storage of medication whereby the user can self-administer the medication in order to vary the dosage delivered. There is no method disclosed in which the time of delivery can be varied by the user in response to erectile requirements.

U.S. Pat. No. 2,577,345 of Mcewen discloses a prophylactic condom having a reinforced cap to prevent breakage of the condom at the tip of the condom. This cap has no internal structure and provides no means for storing or dispensing medications.

U.S. Pat. No. 2,586,674 of Lonne discloses a prophylactic condom with reinforced annular extensions for structural integrity of the condom. The annular protrusions are sealed within the inner and outer layers of the condom and there is no communication between the annular protrusions and the interior cavity of the condom.

U.S. Pat. No. 4,798,600 of Meadow discloses a patent with structural parts designed to stimulate the penis through friction. No structure exists for medication storage or delivery.

U.S. Pat. Nos. 4,432,357; 4,498,466; and 4,564,006, disclose sealed chambers containing a rheopexic material which remains within the chambers. The material is not released from the sealed chamber.

U.S. Pat. No. 4,919,149 of Stang discloses a condom-like device with tubular structures that contain ingestible material that is released upon external stimulus. This ingestible material is delivered to the external environment and not to the interior cavity of the condom-like device. This patent teaches away from the concept of delivering medication or materials into the interior cavity of the condom.

SUMMARY OF THE INVENTION

The present invention includes a sheath and a medication delivery system for facilitating erectile function. The sheath is a member which can be fitted onto a penis. The sheath is open at, at least, one end.

Among the objectives of the invention is that of providing a novel device for stimulating and maintaining erections of the penis by utilizing a transdermal vasodilator medication stored within a fluid retaining chamber and released from that chamber into the interior cavity of the facilitator upon external stimulus.

After the sheath is fitted onto the penis, an external stimulus such as manual compression of the medication containing chamber is administered and a controlled amount of the medication is dispensed into the sheath enabling the user to obtain an erection. If during usage, additional medication is required to maintain the erection, then a second external stimulus can be applied to the one or another of the fluid retaining chambers such that additional medication is dispensed into the sheath without removing the sheath. Multiple doses of medication can thus be administered at different time intervals, thereby providing for a specific individual's penile smooth muscle requirements needed and achieve or maintain an adequate level of erection. Multiple doses and different strength doses can be delivered at different time intervals by the sheath wearer during a single usage episode without removal of the sheath.

BRIEF DESCRIPTION AND DRAWINGS

DESCRIPTION OF THE PREFERRED EMBODIMENT

Figure 1:
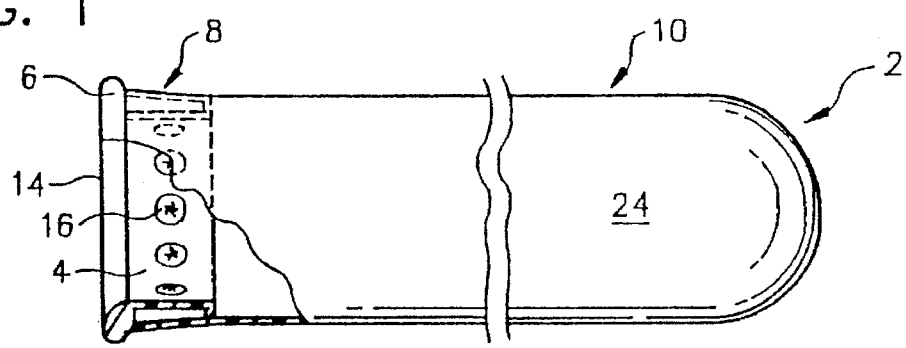
FIG. 1 is a plan view of a first embodiment of the medication dispensing facilitation sheath according to the present invention.
Figure 2:
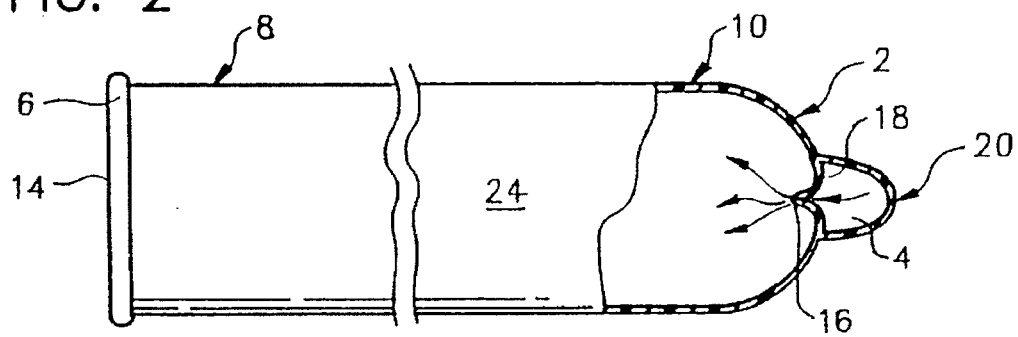
FIG. 2 is a plan view of an alternative embodiment of the facilitator.

Reference is made to FIGS. 1–8 in which facilitators 2 are adapted to dispense materials that include, but are not restricted to, vasoactive medication, (e.g. spermicide, bactericide, anti-viral chemical compounds or the like) onto the surface of the penis. In the preferred embodiments, the materials dispensed are flowable materials. These flowable materials, fluids, include but are not restricted to, liquids, creams, gels, nitrous oxide and colloidal suspensions. Facilitators 2 include a fluid retaining chamber 4 adapted to hold the above types of medications or the like. Oriented at the proximal end 8, a fluid retaining chamber 4 can be located at the base 6 of a facilitator 2 as shown in FIG. 1. Alternatively, fluid retaining chamber 4 can be located at the of the distal end 10 of a facilitator 2, as shown in FIG. 2. The distal end 10 may include the tip 20 of a facilitator 2 as shown in FIG. 2.

Figure 3:
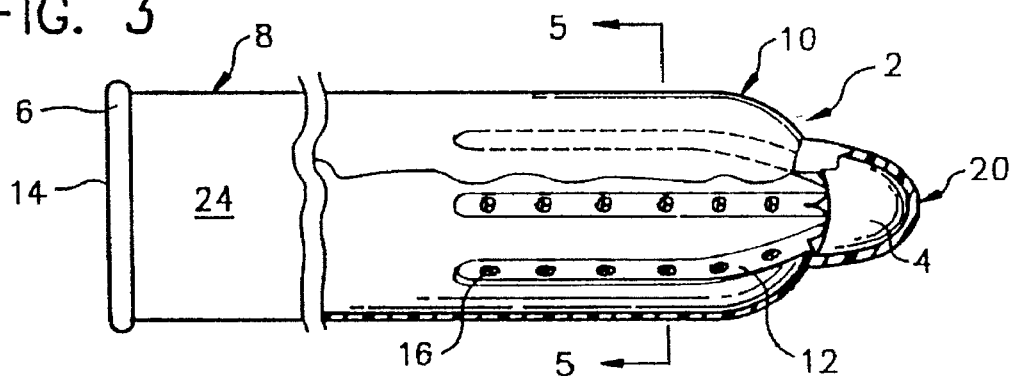
FIG. 3 is a plan view of another alternate embodiment of the facilitator.
Figure 4:
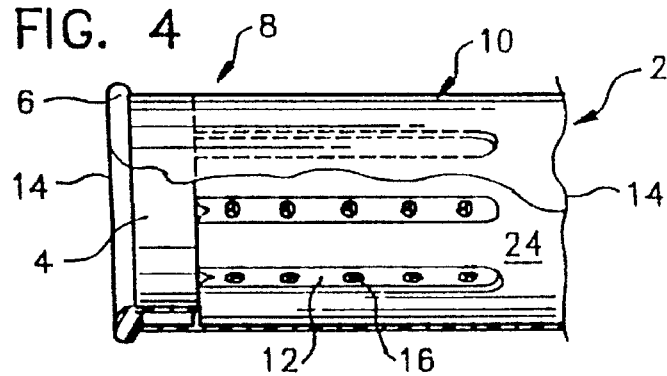
FIG. 4 is a plan view of another alternate embodiment for the facilitator.

Optionally, as shown in FIGS. 3 and 4, a plurality of medication dispensing channels 12 can be oriented on the facilitator 2 with a longitudinal or axial orientation on the facilitator 2. The channels 12 can be in communication with a fluid retaining chamber 4 and can be arranged to increase the area of dispersal of medication or the like through one or more orifices 16 that communicate with the interior cavity 24 of an facilitator 2 and enable passage of medication onto the surface of the penis in the sheath 2.

A facilitator 2 can be open ended as at 14 at its base 6 and closed at its distal end 10. In certain embodiments, that of FIG. 4 being illustrated for example, the facilitator 2 can be open ended as at 14 at both its base 6 and at its distal end 10.

A fluid retaining chamber 4 may be partitioned from the remainder of a facilitator 2 except for communication therebetween by a one-way valve 18 as in the form shown in FIG. 2. One-way valve 18 can be comprised of an orifice 16 surrounded by an area of elastomeric material 22, such as latex or the like which constricts orifice 16 and normally prevents passage of medication or the like from the fluid retaining chamber 4 into the facilitator 2. Other embodiments (not illustrated) can include but are not restricted to, an orifice 16 with a two-way valve, an orifice 16 with an opening covered by a thin yielding membrane, and a minute orifice 16 with no obstructing membranes and no valves. Upon application of external pressure applied to a fluid retaining chamber 4, the pressure within the fluid retaining chamber 4 increases such that orifice 16 is urged open and the medication or the like, flows into the interior cavity 24 of the facilitator 2 and onto the wearer's penis. When channels 12 are present a plurality of orifices 16 as in FIG. 4, for example, may be located therein such that medication or the like in fluid retaining chamber 4 passes from fluid retaining chamber 4 into channels 12 through orifices 16, and into the interior 24 of facilitator 2. In this configuration, the medication or the like may already be contained in channels 12, and optionally in fluid retaining chamber 4 as well, such that application of external pressure onto channels 12 releases the medication or the like. In another embodiment (not illustrated), the channels 12 of the facilitator 2 can contain medication and the channels 12 are not connected to a separate fluid retaining chamber 4. In such an embodiment, the channels 12 serve as the sole fluid retaining chamber or means, and upon external pressure can dispense medication and the like through one or more orifices 16 into the interior 24 of the facilitator 2.

Figure 5:
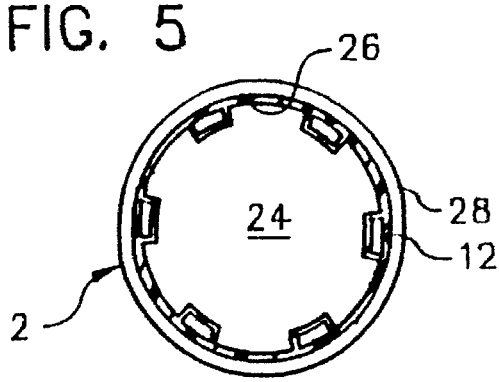
FIG. 5 is a cross sectional view of either of the embodiments shown in FIG. 3 and 4, taken through the facilitator channels.

FIG. 5 is a cross sectional view of embodiments with channels 12 located on the inner surface 26 of the facilitator 2. Additional embodiments (not illustrated) can include arrangements wherein, channels 12 are located between the inner 26 and outer 28 surfaces of the sheath.

Figure 6:
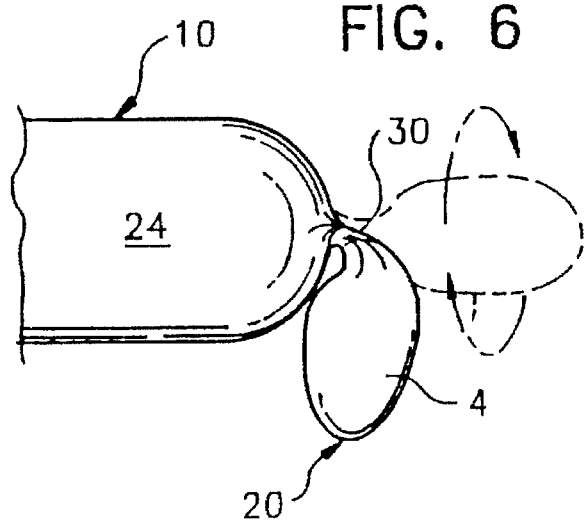
FIG. 6 is a plan view of an alternative embodiment of the closed end and fluid retaining chamber.
Figure 7:
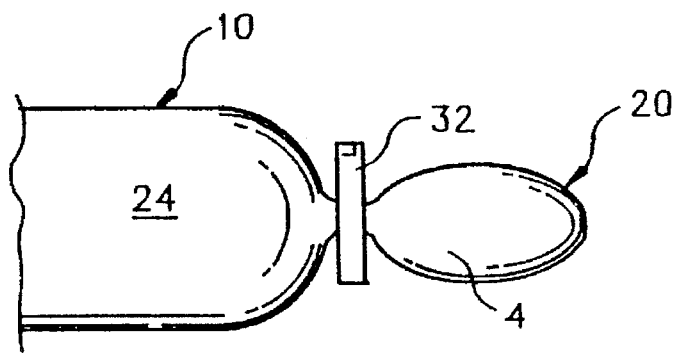
FIG. 7 is another plan view of an alternative embodiment of the closed end and fluid retaining chamber.
Figure 8:
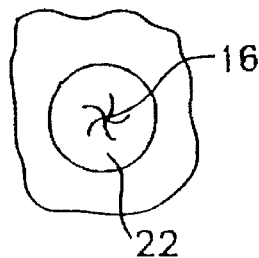
FIG. 8 is a cross sectional view of either of the embodiments shown in FIG. 6 and 7, taken at the neck of the facilitator.

As shown in the embodiments shown in FIG. 6, 7 and 8, medication or the like can he partitioned from facilitator 2 in a fluid retaining chamber 4 by providing the fluid retaining chamber 4 with an elongated neck 30 which is adapted to be folded upon rolling or twisting the end of the facilitator for storage prior to use. In this manner, medication or the like is partitioned from facilitator 2 in fluid retaining chamber 4. When the facilitator is unrolled for use elongate neck 30 is likewise unfolded and the medication or the like in fluid retaining chamber 4 then passes from fluid retaining chamber 4 through an orifice 16 (FIG. 8) that can be surrounded by an elastomeric material 22, and thus delivered into the interior 24 of facilitator 2 and onto the penis. Optionally, as in FIG. 7, an elongate neck 30 can be closed by a clamp or bendable tie 32 to partition facilitator 2 and fluid retaining chamber 4, in lieu of having a folding elongated neck 30 as in FIG. 7.

From the foregoing discussion of various illustrative embodiments of the invention and methods of use thereof, further modifications, variations and adaptations thereof will occur to those skilled in the art to which the invention is addressed, within the scope of the following claims.

What is claimed is:

1. The method of dispensing medication and the like to facilitate male penis erectile function, comprising:
   providing an elastic sheath open at both ends with at least one fluid retaining chamber incorporated therein and with means for initially partitioning and for subsequently providing communication between said at least one fluid retaining chamber and the interior of said sheath such that fluid in said fluid retaining chamber can be dispensed into the interior of said sheath by the application of external pressure to said at least one fluid retaining chamber;
   installing said elastic sheath onto the penis of a person needing erectile function facilitation, and dispensing, under control of the wearer of said elastic sheath, the medication or the like to the interior of said elastic sheath and onto the wearer's penis by the wearer applying external pressure to said at least one fluid retaining chamber as and when needed for such facilitation.

2. The method of claim 1, comprising arranging said at least one fluid retaining chamber in the proximal portions of said elastic sheath and applying external pressure to said proximal portions.

3. The method of claim 1, comprising arranging said at least one fluid retaining chamber in the distal portions of said elastic sheath and applying external pressure to said distal portions.

4. A facilitator for dispensing flowable medication or the like onto a penis, comprising:

an elastic sheath open at both ends and adapted to fit onto a penis;

at least one fluid retaining chamber incorporated in said elastic sheath; and means for initially partitioning and for subsequently providing communication between said at least one fluid retaining chamber and the interior of said elastic sheath such that fluid in said fluid retaining chamber can be dispensed into the interior of said sheath.

5. The facilitator of claim 4, wherein said elastic sheath comprises a plurality of channels connected with said fluid retaining chamber, each of said channels including said means for initially partitioning and for subsequently providing communication between said fluid retaining chamber and said elastic sheath, said channels also being adapted to store fluid prior to dispensing the fluid into the interior of said sheath.

6. The facilitator of claim 4, wherein said fluid retaining chamber comprises a plurality of channels, each of said channels including said means for initially partitioning and for subsequently providing communication between said channels of said elastic sheath, said channels being adapted to store fluid such that the fluid can be dispensed into the interior cavity of said facilitator.

7. The facilitator of claim 4, wherein said elastic sheath has a base portion and said fluid retaining chamber is in said base portion.

8. The facilitator of claim 4, wherein said elastic sheath has a distal portion and said fluid retaining chamber is in said distal portion.

9. The facilitator of claim 4, wherein said means for initially partitioning and for subsequently providing communication between said sheath and said elastic fluid retaining chamber comprises valve means openable responsive to pressure and comprising a region of elastomeric material whereby said area of elastomeric material is expandable by application of external pressure on the fluid in said retaining member to open said orifice such that the fluid passes therethrough and into said elastic sheath.

\* \* \* \* \*